United States Patent [19]

Bizub et al.

[11] Patent Number: 4,957,859

[45] Date of Patent: Sep. 18, 1990

[54] ANTIBODIES FOR TRANSFORMING RAS PROTEIN

[75] Inventors: Diane Bizub, Glenside, Pa.; Ellyn Fischberg-Bender, Ossing, N.Y.; Anna M. Skalka, Princeton, N.J.

[73] Assignee: Hoffmann-La Roche Inc., Nutley, N.J..

[21] Appl. No.: 156,133

[22] Filed: Feb. 16, 1988

[51] Int. Cl.$^5$ .................. G01N 33/53; G01N 33/543; G01N 33/544
[52] U.S. Cl. ........................................ 435/7; 530/387; 436/548; 436/501; 436/518; 436/530; 436/536; 436/538; 935/104; 935/110
[58] Field of Search .................. 530/300, 333, 387; 435/68, 172.2, 7; 436/548, 501, 518, 534, 536, 538

[56] References Cited

U.S. PATENT DOCUMENTS 4,786,718 11/1988 Weinberg et al. .................. 530/387

FOREIGN PATENT DOCUMENTS 177814A 4/1986 European Pat. Off. .

OTHER PUBLICATIONS

Cetus Diagnostics Brochure, Mouse Monoclonal Antibody.
Guenero et al., PNAS 82, pp. 7810-7814, 1985.
Bizub et al, PNAS 83, pp. 6048-6052, 1986.
Lerner, Nature, 299, pp. 592-596, 1982.
Clark et al., Proc. Natl. Acad. Sci., USA 82, pp. 5280-5284, (1985).
Niman et al., Proc. Natl. Acad. Sci., USA 82, pp. 7924-7928, (1985).

*Primary Examiner*—Christine Nucker
*Assistant Examiner*—Karen I. Krupen
*Attorney, Agent, or Firm*—George M. Gould; William H. Esptein; John J. Schlager

[57] ABSTRACT

Preparation of novel polypeptide sequences spanning amino acid position 61 of the ras protein, said sequences being characterized as containing a leucine in that position instead of the glutamine found in normal ras protein, the utilization of such polypeptides to prepare immunogen compositions utilizing such polypeptide covalently linked to immunogenic carrier materials, the production of antibodies elicited by such polypeptides, the screening of such antibodies to provide monoclonals specific to the P21Tleu61 transforming protein and to immunoassay and use in immunochemical methods employing such antibodies to determine the presence of the p21TLeu61 transforming protein.

11 Claims, No Drawings

ANTIBODIES FOR TRANSFORMING RAS PROTEIN

BACKGROUND OF THE INVENTION

The preparation of monoclonal antibodies using synthetic polypeptides derived from the variable regions of p21 ras proteins encoded by the family of oncogenes designated ras[H], ras[K], and ras[N] was described in U.S. Pat. application Ser. No. 739,416, filed May 30, 1985, entitled RAS ONCOGENE PEPTIDES AND ANTIBODIES, inventors Chizzonite et al. These polyclonal antibodies are each selective for the specific family from whose sequence the immunogenic peptide was synthesized. Thus the antibodies can be used to assay for the presence of the specific ras gene products in a biological fluid specimen.

It is also known in the art to provide ras oncogene antibodies which are selective for the substitution of an amino acid at position 12 of the ras p21 protein. Thus, for example, an anti-p21-ser rabbit polyclonal antibody which binds to v-Ki-ras (serine at position 12) but not to v-Ha-ras (arginine at position 12) protein is an article of commerce (Cetus Diagnostics, Emeryville Calif). Also available are polyclonal antibodies specific for polypeptides with the following changes at position 12: Val, Asp and Arg. These antibodies are provided in kit format useful for analysis of cellular and tissue extracts for the presence of the corresponding mutant proteins. The mutant proteins are thought to facilitate the transformation process in human tumors. Additionally, a monoclonal antibody which is directed against the conserved regions of p21 ras protein thus serving as a pan antibody reactive with all known forms of the p21 protein is also an article of commerce. The pan reactive antibody is indicated to be useful for exploring ras oncogene expression. The preparation of such materials is described by Clark et al., Proc. Natl. Acad. Sci. USA 82, 5280–5284 (1985).

Another changed position in p21ras oncogenes is known to provide proteins that facilitate the transformation process in human tissues. This involves mutation at codon 61 in the p21 ras sequence to provide leucine instead of the glutamine contained in the normal sequence. A monoclonal antibody which could selectively recognize such a change would be extremely useful in identifying the p21Leu61 transforming protein in cells, tissues and biological fluids.

SUMMARY OF THE INVENTION

The present invention relates to the preparation of novel polypeptide sequences spanning amino acid position 61 of the ras protein, said sequences being characterized as containing a leucine in that position instead of the glutamine found in normal ras protein, the utilization of such polypeptides to prepare immunogen compositions utilizing such polypeptides covalently linked to immunogenic carrier materials, the production of antibodies elicited by such polypeptides, the screening of such antibodies to provide monoclonals specific to the p21TLeu61 transforming protein and to immunoassay and use immunochemical methods employing such antibodies to determine the presence of the p21 TLeu61 transforming protein. Since this sequence is conserved among the three members of the ras family (ras[H], ras[K], ras[N]) in both human and mouse proteins such monoclonal can be used as a pan-reactive antibody for p21TLeu61 transforming proteins. A further embodiment of the present invention involves generation of monoclonal antibodies that recognize the normal ras p21 protein and the p21 TLeu61 transforming ras p21 protein equally well. As the region in the vicinity of the 61st codon is conserved among all members of the ras proto-oncogene family, such monoclonal antibodies can be used as pan-reactive p21 antibodies recognizing both normal and mutant protein.

DESCRIPTION OF THE INVENTION

A first aspect of the present invention relates to the preparation of polypeptides derived from the sequence spanning position 61 of the ras p21 protein with the normal amino acid glutamine or the mutant substituent leucine at position 61. Most preferably the polypeptides of the present invention comprise the following specific sequences:

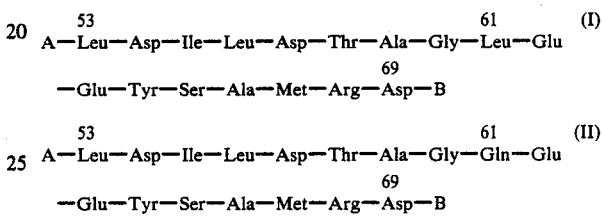

where A is H— or an amino acid having a side chain functional group capable of covalently binding to an immunogenic carrier material and B is —OH or an amino acid having a side chain functional group capable of covalently binding to an immunogenic carrier material.

Sequence I represents a sequence spanning position 61 of the mutant proteins ras p21 which contain Leu at position 61 whereas Sequence II represents a sequence spanning position 61 of the normal ras p21 protein which contain Gln at position 61. It is within the skill of the art to utilize sequences spanning position 61 of ras p21 protein which are shorter, longer or disposed to the amino or carboxy terminus of the ras p21 protein from those provided as specific embodiments in sequences I and II and such alternate sequences are part of the present invention.

The above specific or alternative sequences can be synthesized utilizing peptide synthesis procedures well known in the art. Such procedures include solution phase synthesis and solid phase synthesis, the latter for example, applying the methodology developed by Merrifield, J. Am. Chem. Soc. 85, 2149 (1963). The preferred methodology for synthesizing the peptides of the present invention is the solid phase method which employs cyclic additions of amino acids to the carboxy terminal amino acid of the peptide desired to be synthesized covalently bound to a conventional solid phase synthesis resin. Suitable resins for this purpose are articles of commerce and include for example cross-linked polystyrene resins. Such resins can now be obtained commercially with the desired carboxy terminal amino acid already covalently linked to the resin. The added amino acids can be protected with conventionally employed side-chain protecting groups. Suitable side-chain protecting groups for this purpose include benzyl, benzyloxycarbonyl, chlorobenzyl, p-chloro-benzyloxycarbonyl, toluenesulfonyl or dimethyl benzyl.

Peptides of sequence I or II where A and/or B is an amino acid having a side chain functional group capable of covalently binding to an immunogenic carrier material are especially preferred as immunogens for eliciting monoclonal antibodies of the present invention. Suitable amino acids for use as an A and/or B substituent group include Cys, Lys, Trp. A preferred amino acid for A and/or B substituent group is Cys. In a most preferred embodiment, mixtures of peptides are used where either A or B are Cys. It is understood of course that if an amino acid is used for A and/or B substituent group they do not constitute a part of the sequence of the ras p21 protein but are functioning as linking groups.

The above described polypeptides preferably after purification by a method known per se, such as high performance liquid chromatography, can be employed as immunogens to prepare the specific antibodies of the present invention. Such immunogens are readily obtained by covalently binding each of the above described polypeptides to a conventional immunogenic carrier material. The term "immunogenic carrier material" is meant to include those materials which have the property of independently eliciting an immunogenic response in a host animal and which can be covalently coupled to the aforesaid polypeptides either directly by the formation of peptide or ester bonds between free carboxyl, amino or hydroxyl groups in the aforesaid polypeptides and corresponding groups on the immunogenic carrier material, by coupling through the sulfhydryl group of the Cys moiety or alternatively by binding through a conventional bifunctional linking group.

The covalent coupling of the polypeptides of the invention to the immunogenic carrier material can be carried out in a manner well known in the art. Thus, for example, for direct covalent coupling, it is possible to utilize a carbodimide, most preferably dicyclohexyl carbodimide or 1-ethyl-3-(3-dimethylaminopropyl) carbodimide as coupling agent. In such direct coupling, it is desirable to utilize a slightly acidic reaction medium for this step, e.g., a medium having a pH in the range of from about 3 to 6.5, most preferably in the range of from about 4 to 6.5.

A suitable bifunctional linking group for effecting coupling is a $C_{2-7}$ dialkanal such as glutaraldehyde. Such coupling in this alternative embodiment can conveniently be carried out using the conditions described by S. Avrameas, Immunochemistry 6, 43 (1969).

Still another preferred reagent for use in coupling of the polypeptides of the present invention to the immunogenic carrier material is m-maleimidobenzoyl N-hydroxysuccinimide (MBS) which can be utilized at room temperature in an aqueous soluble solvent such as for example dimethylformamide (DMF). It is preferred to utilize the immunogenic carrier material dissolved in a suitable phosphate buffer at pH 7.2.

The resulting immunogen can be utilized without further purification or, if desired, after purification by procedures well known in the art, such as, for example, dialysis to remove any unreacted peptide and coupling reagents or alternatively by use of column chromatography on a suitable column, e.g., Sephadex G-25.

Suitable carrier materials which can be used in the preparation of the immunogens of the instant invention include proteins, natural or synthetic polymeric compounds such as polypeptides, e.g., polylysine or copolymers of amino acids; polysaccharides; and the like. Particularly, preferred carrier materials are proteins and polypeptides, especially proteins.

The identity of the protein utilized in the preparation of an immunogen of the instant invention is not narrowly critical. Examples of suitable proteins include mammalian serum proteins such as, for example, human gammaglobulin, human serum albumin, bovine serum albumin, methylated bovine serum albumin, rabbit serum albumin, bovine gammaglobulin, bovine thyroglobulin and equine gammaglobulin or nonmammalian proteins such as hemocyanin, most preferably keyhole limpet hemocyanin. Other suitable proteins will be suggested to one skilled in the art.

The immunogens of the present invention may be utilized to induce formation of antibodies specific to the respective normal and mutant ras P21TLeu61 proteins in host animals by injecting the immunogen in such a host, preferably using an adjuvant. Improved titers can be obtained by repeated injections over a period of time. Suitable host animals for this purpose include mammals such as rabbits, guinea pigs, horses, goats, rats, mice, cows, sheep, etc. The resulting antisera contain antibodies which will selectively complex with the respective oncogene proteins. Such sera can be utilized per se in carrying out assays for such oncogene protein, or if desired, the antibody can be concentrated by utilizing procedures well known in the art such as, for example, by ammonium sulfate precipitation followed by gel chromatography. In an alternative but preferred embodiment of the present invention, monoclonal antibodies useful in the detection of the mutant ras p21 proteins may be obtained by known methodologies available in the art such as, for example, those described by Milstein and Kohler as described in Nature, 256, 495–497, 1975. In such a procedure, the immunogens of the present invention are injected into a mouse or a rat. The host animal is subsequently sacrificed and cells taken from its spleen are fused with myeloma cells. The result is a hybrid cell, referred to as a "hybridoma", that reproduces in vitro. The population of hybridomas are screened to isolate individual clones, each of which secretes a single antibody species against the antigen polypeptide which was used as the immunogen. The individual antibody species obtained in this way are each the product of a single B cell from the immunized animal generated in response to a specific antigenic site recognized on the immunogenic substance. In this instance, since a subsequence of the normal or mutant protein was employed, the antibody will be specific not only to the subsequence but also to the full protein as well. Moreover while the monoclonal antibodies to the normal peptide sequence recognize both the normal and mutant p21 proteins the monoclonal antibody raised against the mutant peptide selectively binds to the mutant protein but not to the normal protein.

The different hybridoma cell lines are then screened to identify those that produce antibody to the desired antigen. The antibodies produced by the individual hybridoma cell lines are preferably screened to identify those having the best affinity and avidity for the immunogenic substance stimulating their original production before selection for use in the present invention.

The monoclonal antibodies produced in accordance with the present invention can be utilized in any conventional immunometric assay for use in detecting the presence of the respective ras p21 proteins in test samples preferably human tissues or biological fluids such as urine, blood, tissue extracts, saliva and the like. In one such procedure, known amounts of a sample to be assayed, the specific antibody of the present invention and labeled ras p21 normal or mutant (transforming) polypeptide or protein are mixed together and allowed to stand. The antibody-antigen complex is separated from the unbound reagents by procedures known in the art, i.e., by treatment with ammonium sulfate, polyethylene glycol, or second antibody either in excess or bound to an insoluble support. Suitable insoluble supports include polymers such as Kynar, dextran coated charcoal and the like. The concentration of the labeled ras polypeptide or protein is determined in either the bound or unbound phase and the specific ras p21 protein content of the sample can then be determined by comparing the level of labeled component observed to a standard curve in a manner known per se. A suitable standard curve can be obtained by mixing known amounts of ras p21 protein with fixed amounts of labeled ras p21 protein and the ras p21 specific antibody of the present invention and determining the degree of binding for each such known amount. Since the antibodies of the present invention can distinguish between the normal and transforming forms of the ras p21 protein, it is possible to determine the presence of the mutant forms of the ras oncogene protein and quantitate their levels in the presence of other forms of the protein.

Use of two different monoclonal antibodies specific for the normal or transforming ras oncogene protein, which antibodies do not interfere with the binding of each other to the antigen may be employed in a two-site immunometric assay procedure. Suitable homogenous and heterogenous two-site immunometric assay procedures are described in U.S. Pat. No. 4,376,110.

Yet another immunometric methodology which can be employed in the practice of the present invention involves the use of an immunoblot technique. In this technique, samples containing the ras p21 protein are mixed with SDS sample buffer, with or without 2-mercaptoethanol as a sulfhydryl reducing reagent, boiled and electrophoresed on polyacrylamide gels. Proteins are electrophoretically transferred to nitrocellulose filters using a "Transblot" apparatus following the procedure described by H. Towbin, T. Staehelin, J. Gordon, 1979, Proceedings of the National Academy of Sciences, U.S.A., Vol. 76, pages 4350–4354 in an article entitled "Electrophoretic Transfer of Proteins From Polyacrylamide Gels to Nitrocellulose Sheets: Procedure and Some Applications". After preincubation with buffered bovine serum albumin, the filters are incubated overnight with antiserum to the desired human ras p21 protein. The filters are then washed and incubated sequentially with appropriate labeled antisera directed against the IgG of the species in which the ras specific antibody was developed. Such second antibody can be labeled with any conventional label such as a radioisotope or preferably with an enzyme such as with peroxidase. The filters may then be washed again and incubated with an appropriate substrate for the enzyme such as, for example, with diaminobenzidine until the protein bands are observed. The absence of color bands with any antibody specific for the normal or transforming human ras p21 protein would indicate the absence of such protein in the test sample. If one desires only to know whether or not ras protein is present in the test sample, then use of the pan-specific antibodies may be employed. If, on the other hand, the presence or absence of the transforming ras protein is to be determined, then the mutant antibodies specific for this mutant ras protein would be employed on repetitive test samples.

The antibodies of the present invention may also be utilized in heterogenous "sandwich" type assays. In such a heterogenous assay, an unlabelled antibody, preferably a monoclonal antibody, is used to extract the test protein substance from the sample and such antibody is immobilized on any of the conventional supports used in immunometric assays. Among these supports, there is included, filter paper, plastic beads or test tubes made from polyethylene, polystyrene, polypropylene or other suitable material. Also useful for this purpose are particulate materials such as agarose, cross-linked dextran and other polysaccharides. The techniques for such binding are well known to those skilled in the art. For example, antibodies may be bound to polysaccharide polymers using the process described in U.S. Pat. No. 3,645,852.

Labeled specific antibody used in the present invention may be provided with the same labels used in immunometric assays known in the art. Among these may be mentioned fluorogenic labels for detection by fluorimetry as described in U.S. Pat. No. 3,940,475 and enzymatic markers as described in U.S. Pat. No. 3,645,090. It is also possible to utilize a radiolabeled antibody such as, for example, $I^{125}$ using, for example, the procedure of Hunter and Greenwood, Nature 144, (1962), p. 945 or that of David et al., Biochemistry, Vol. 13, pp. 1014–1021, (1974).

In a typical heterogenous sandwich assay, the amount of labeled antibody associated with the insoluble sandwich complex is determined by examination of the insoluble carrier material by suitable means. However, it is also possible to relate the presence or absence of the test protein in the fluid sample being assayed to the amount of labeled antibody which does not react during the assay and remains in a soluble form.

In yet another embodiment of the present invention, the antibodies of the invention can be used for antibody affinity chromatography purification of the respective ras proteins to which they react specifically. For this purpose, the antibodies are immobilized on a matrix in a manner known per se, suitably covalently bound to a suitable antibody affinity chromatography matrix such as a cross-linked agarose such as Sepharose IVB commercially available from Pharmacia. The antibody affinity chromatography purification of human ras protein from various sources may be performed according to any of the well known methods, either batchwise or, preferably, using the matrix-immobilized antibody arranged on a column.

DESCRIPTION OF THE PREFERRED EMBODIMENT

The three members of the ras proto-oncogene family, H-, K-, and N-ras, encode highly conserved 21 kDa proteins (p21). See for example Capon et al., Nature, 302, 33–37 (1983). DNA isolated from a variety of animal and human tumors can transform NIH3T3 cells and a large percentage contain activated ras genes with single base changes at the 12th or 61st condon. The mouse skin tumor model has been used to study carcinogenesis. In this model, it has previously been shown that about 80% of the papillomas and carcinomas induced by DMBA and DB(ch)ACR contain activated H-ras oncogenes containing an AT transversion (mutation) at the second position of the 61st condon, Bizub et al., Proc. Natl. Aca. Sci. USA, 83. 6048–6052 (1986). In the mutant transforming gene, Leu replaces Gln at condon 61. It has also been shown by immunohistochemical staining that the H-ras gene is highly expressed in these same tumors; however, it was not possible to distinguish between the normal and transforming proteins, Bizub et al., Oncogene, 1, 131-142 (1987).

In order to be able to detect the transforming gene specifically, it has been necessary to develop a monoclonal antibody against a suitable peptide, preferably codons 53 to 69, which contains the single amino acid change. This region is otherwise conserved among human H-,K-,N-ras, Capon, et al. supra and mouse H-,K-,N-ras, Guerrero et al. Proc. Natl. Acad. Sci. USA, 82, 7810-7814 (1985). Therefore such an antibody would be useful in detecting this activating mutation in H-,K-, or N-ras proteins. As will be seen in the following examples, a monoclonal antibody having the characteristics of the monoclonal antibody ras(53-69) Leu61 which represents a preferred embodiment of the invention selectively reacts with the transforming but not the normal ras p21 protein in immunoblotting and immunohistochemical staining of tissue culture cells.

EXAMPLE 1

Preparation and conjugation of Peptides. The synthesis of the peptides used for immunization was performed by the Merrifield solid-phase methodology The Peptide: Analysis, Synthesis, Biolig; G. Barany and R. B. Merrifield; Gross and Meinhofer, Ed.; Academic Press, N.Y.; Vol. 2 pp1-384 (1980). The crude preparations were purified to homogeneity by preparative high-pressure liquid chromatography using the procedure of Felix et al., Int. J. peptide protein Res., 26, 130-148 (1985) and gave the expected amino acid composition after acid hydrolysis. The peptide (4 mg) was coupled to the carrier protein, keyhole limpet hemocyanin (KLH) (5mg), using m-maleimidobenzoyl-N-hydroxysuccinimide as the linking agent. The conjugation and subsequent work-up was performed as described by Green et al. Cell, 28, 477-487 (1982).

I Synthesis of H-Leu-Asp-Ile-Leu-Asp-Thr-Ala-Gly-Gln-Glu-Glu-Tyr-Ser-Ala-Met-Arq-Asp-Cys-OH Solid-phase peptide synthesis was carried out in an upright vessel clamped to a Model S-500 shaker equipped with an RD-20 shaker head (Kraft Apparatus, Inc. Minniola, N.Y.) using a manual procedure. Cys (Dmb) —1% cross linked polystyrene (200-400 mesh) resin (4g, 0.48 mmole/g resin) was subject to 17 cycles of solid phase peptide synthesis using the preformed symmetric anhydride procedure. A portion of the final protected peptide resin (1.2g) was treated with anhydrous liquid HF (20 mL containing 10% dithioethane) at 0° for 1 h and evaporated (high-vac, CaO trap). The crude peptide and resin mixture was triturated with EtOAC, extracted with TFA, evaporated, triturated with ether and dried to give 510 mg. A portion of the crude product (301 mg) was dissolved in distilled water; filtered and cooled into a Nucleosil C$_{18}$ 5$\mu$ column (2.5×25 cm). The column was eluted (5 mL/min) with a solvent system consisting of (A) H$_2$O (containing 0.1% TFA) (B) CH$_3$CN (containing 0.1% TFA) in a lunear gradient mode: 10-35% (B) in 150 min. Fractions were collected (every minute) and aliquots analyzed using an analytical hplc system. The fractions containing the product were combined, evaporated and lyopilized to give the pure peptide: 33 mg. The product was shown to be homogeneous by analytical hplc and gave the expected amino acid composition: (6 NHCl, 110°, 24 h): Asp, 3.06; Ser, 1.02; Glu, 3.15; Gly, 0.95; Ala, 2.00; Met, 1.05; Ile, 0.80; Leu, 1.86; Tyr, 1.10; Arg, 1.04.

II Synthesis of Cys-Leu-Asp-Ile-Leu-Asp-Thr-Ala-Gly-Gln-Glu-Glu-Tyr-Ser-Ala-Met-Arg-Asp-OH Asp (O Bzl)-1% cross-linked polystyrene resin (5.0 g, 0.39 mmol/g-resin) was subjected to 17 cycles of solid-phase peptide synthesis, cleared with anhydrous HF and purified as in I above. The product was shown to be homogeneous by analytical hplc and gave the expected amino acid composition; (6 NHCl, 110°, 24 h): Asp, 3.01; Thr, 0.96; Ser, 0.92; Glu, 3.12; Gly, 1.03; Ala, 2.04; Met, 1.92; Ile, 0.96; Leu, 2.03; Tyr, 1.01; Arg, 1.01.

III Synthesis of Leu-Asp-Ile-Leu-Asp-Thr-Ala-Gly-Leu-Glu-Glu-Tyr-Ser-Ala-Met-Arg-Asp-OH Boc Asp(OBzl)-resin (2g, 0.5 mmol/g-resin) was charged into the reaction vessel on the Vega model 1000 peptide synthesizer and 17 cycles of solid phase peptide synthesis performed. A 1g-portion of the assembled protected peptide resin was cleared with HF and purified as in I above. The final product was homogeneous by analytical hplc and gave the expected amino acid composition.

IV Leu-Asp-Ile-Leu-Asp-Thr-Ala-Gly-Leu-Glu-Glu-Tyr-Ser-Ala-Met-Arg-Asp-Cys-OH

Boc Cys(4-methylhenzyl)-resin (2g. 0.65 mmol/g-resin) was subjected to 17 cycles of solid phase peptide synthesis, cleared with anhydrous HF and purified as in I above. The purified product was shown to be homogeneous by analytical hplc and gave the expected amino acid composition.

IV Conjugation of H-Leu-Asp-Ile-Leu-Asp-Thr-Ala-Gly-Leu-Glu-Glu-Tyr-Ser-Ala-Met-Arg-Asp-Cys- and Cys-Leu-Asp-Ile-Leu-Asp-Thr-Ala-Gly-Leu-Glu-Glu-Tyr-Ser-Ala-Met-Arg-Asp- with Keyhole Limpet Hemocyanin Keyhole limpet hemocyanin, (Calbiochem 12 mg in 50% glycerol) was added to a solution of m-maleimidobenzoyl-N-succinimide ester (2.1 mg) in DMF (0.2 mL) at 25° and stirred (magnetically) for 30 minutes. The reaction mixture was charged onto a Sephadex G-25 column (1.2×50 cm) which was previously equilibrated with 0.05M NaH$_2$PO$_4$ (pH 6.0). Fractions (1 mL/min) were collected and the first major peak (280 nm detection) was pooled [MB-KLH complex]. The title peptides (5mg of each) were added to one-half of the [MB-KLH complex] in 1 mL of 0.05M NaH$_2$PO$_4$ (pH6) buffer and the pH of the reaction mixture was adjusted to 7-7.5 by additions of 1N NaOH (ml amounts) and stirring proceeded at 25° overnight. The reaction mixture was dialyzed (MW cut-off 3500) against Dulbecco's Phosphate Buffered Saline, with repeated changes at 4° over a 72 hour period. The dialyzed solution (18 mL) was used directly for antibody generation.

EXAMPLE 2

Construction of the P21TLeu61 Expression Vector. A modification of the previously reported in vitro mutagenesis method was used to construct an expression vector to produce H-ras p21 protein containing an AT transversion at the second position of the 61st condon. See Moringa et al., Biotechnology, 2, 636-639 (1984). A small restriction fragment was isolated from a clone containing the genomic H-ras oncogene which contained this mutation for use in the mutagenesis procedure. The exon 2 AccI-FspI fragment (64 base pairs) was mixed with linearized (PvuII) and gapped (HindIII) DNA from pJCL-33, the expression vector constructed by Lacal et al. Proc. Natl. Acad. Sci. USA 81, 5303-5309 (1984), which produces the normal H-ras p21 in bacterial cells. The mixture was denatured and renatured so that the mutated fragment could anneal to the gapped DNA from the expression vector. The DNA was repaired by the Klenow fragment of DNA polymerase I, ligated and used to transform an E. coli expression clone carrying the plasmid pRK248cits, Crowel et al., Gene 38. 31-38 (1985) which encodes the temperature sensitive lambda phage repressor protein. Plasmid DNA from individual colonies was screened by digestion with XbaI which recognizes the AT transversion at condon 61 as previously reported by Bizub et al. Proc. Natl. Acad. Sci. USA, 83, 6048-6052 (1986). H-ras p21 protein was synthesized in E. coli and protein was isolated by a modification of Manne et al. Proc. Natl. Acad. Sci. USA, 81, 5303-5309 (1984) using 8M urea for extraction.

EXAMPLE 3

Immunization Protocol. Female Balb/C mice (Jackson Laboratories), approximately 12 weeks of age, were immunized by i.p. inoculation with 100 mgs of KLH coupled peptide mixed 1:1 with complete Freud's adjuvant (Gibco Laboratories, Grand Island, N.Y.). The mice were also immunized with 50 $\mu$l of *Bordetella pertussis* (Difco) i.m. in the hind leg. Additional immunizations were performed at 6 and 10 weeks after primary injection, using 100 $\mu$gs of KLH coupled peptide mixed 1:1 with incomplete Freud's adjuvant. The mice were allowed to rest for 5 month. All serum samples were tested for the presence of anti-peptide antibodies by ELISA assay as in Bizub et al. Oncogene, 1, 131-142 (1987). Ninety-six well microtiter plates (Immulon II, Dynatech) were coated With 100 ngs of normal and mutant peptide or 400 ngs of normal or transforming p21 protein per well. By ELISA assay, the mouse picked for use in fusion had a four fold higher serum titer on p21TLeu61 protein than on normal p21 protein.

EXAMPLE 4

Fusion. On day 4, 3, and 2 before fusion, the chosen mouse was immunized by i.p. inoculation with 400 $\mu$gs, 200 $\mu$gs, and 200 $\mu$gs (Staehli et al., J. Imm. Methods, 32. 297-304 (1980)) respectively, of conjugated peptide in PBS. On day 1, the spleen was removed and the cells fused using the method of Facekas et al., J. Imm. Methods, 35, 1-21 (1980) with the NSO myeloma line described by Galfri and Milstein, Methods in Enzymology part C 73, 3-46 (1981) Cells were seeded into 25-96 well tissue culture plates at a concentration of $2.5 \times 10^5$ NSO cells/ml in HAT media. After 10 days to 2 weeks, supernatants were removed and tested by ELISA assay for binding to the transforming protein but not the normal H-ras p21 protein. Supernatant from only one well was found to recognize the transforming and not the normal p21 protein. The cells from the positive well, ras(53-69)Leu61 mAb, was cloned twice in soft agar as per Coffino et al. J. Cell. Physiol. 79 (1972). Ascites fluid was prepared by inoculating $5 \times 10^6$ cells/mouse in $CAF_1/5$ mice (Jackson Laboratories) as described by Kwan et al., Genetic Engineering, eds. Settoro & Hollaender (Plenum Publishing Corp., N.Y.) pp 31-45 (1980).

EXAMPLE 5

Purification of ras(53-69)Leu61 Monoclonal Antibody. Five mls of ascites fluid from mice innoculated in Example 4 were clarified by centrifugation at 2000 rpm for 10 min using a Beckman JA 17 rotor. The AffiGel protein A Maps II Kit (Biorad, Rockville Centre, N.Y.) was used to purify the antibody according to the manufacturer's specifications. The eluted antibody was dialysed against PBS (25 mM $NaPO_4$, 150 mM NaCl, pH 7.2). Protein concentration was determined by use of the Biorad Protein Assay Kit. ELISA assay was used to titer the purified antibody.

EXAMPLE 6

Growth, Fixation, and Immunohistochemical Staining of Tissue Culture Cells. Cells were grown overnight on 4 chamber Lab-Tek tissue culture slides seeded at $2 \times 10^4$ cells well (Miles Laboratories, Inc., Naperville, Ill.) and fixed with methanol as described by Furth et al. J. Virol. 43, 294-304 (1982). The Vectastain ABC kit (mouse IgG) (Vector Laboratories, Burlingame, Calif.) was used in peroxidase staining of tissue cultures following the procedure of Bizub et al., Oncogene, 1, 131-142 (1987).

Immunoblotting with affinity purified ras(53-69-)Leu61 mAb was carried out as follows. Purified bacterially-produced normal and transforming (Leu61) H-ras proteins were mixed with $2 \times$ SDS sample buffer, boiled for 5 min and fractionated by electrophoresis through a 12.5% polyacrylamide gel. Immunoblots were aligned with prestained BRL (Gaithersburg, MD) low molecular weight markers. The purified transforming protein and the normal p21 protein were stained with Commassie blue. Proteins from Panels B and C were transferred to nitrocellulose filters (0.22 $\mu$m) using the Transblot apparatus (Hoeffer) according to the manufacturer's specification. The filters (Panels B and C) were incubated with 3% gelatin in PBS and 0.02% $NaN_3$ at 37° C., overnight. After rinsing with PBS, the filter in Panel B was incubated with the rabbit affinity purified H-ras(171-189) specific antibody. The rabbit polyclonal antibody was diluted to 1 $\mu$g/ml in PBS and incubated with the filter in Panel B for 3.5 hrs at room temperature with gentle shaking. The filter from Panel C was incubated with affinity purified ras(53-69)Leu61 mAb diluted to 75 $\mu$g/ml in PBS for 2.5 hrs at room temperature with gentle agitation. It was then rinsed with PBS and incubated with goat anti-mouse IgG antibody (Boehringer Mannheim Biochemicals, Indianapolis, Ind.) diluted 1/500 in PBS and 0.2% BSA and incubated for 2 hrs at room temperature with gentle agitation. Filters of Panels B and C were washed in PBS and 0.05% $Tween_{20}$ at room temperature for 15 min. The filters were incubated with $^{125}I$ protein G (12 mCi/$\mu$g) (Amersham. Arlington, Ill.) diluted 1/1000 in antibody buffer, ph 6.5 (20 mM $NaPO_4$, 0.5M NaCl, 0.05% $Tween_{20}$, 1% BSA, 0.02% $NaN_3$) at room temperature for 2 hrs with gentle agitation. They were washed with 4 changes of PBS and 0.05% $Tween_{20}$ at room temperature for 15 min, wrapped in Saran Wrap, and exposed to preflashed Kodak XAR5 film with a Lighting plus screen for 2 days at −70° C. The Commassie Blue stained gel and the autoradiograms corresponding to Panels B and C, were photographed at the same magnification so proteins could be aligned.

DISCUSSION

Preparation of the Monoclonal Antibody. The sequence of ras, from amino acid 53 to 69 is given above where A is H and B is OH in sequence II. The normal ras p21 sequence contains Gln at codon 61. The amino acid sequence of this region is conserved among all members of the ras gene family in both mouse and man. The transforming sequence (T). differs at the 61st condon where Leu replaces Gln as seen above where A is H and B is OH in sequence I. Two peptides were synthesized for the T sequence where Cys was either added to the amino- or carboxyl- termini. This was based on the observation that some peptides were more immunogenic if coupled to Cys at the amino- terminus while others were immunogenic if coupled to the carboxyl terminus. To increase the probability of antibody production, both peptides were prepared, pooled, and conjugated to KLH. Ten mice were injected with the peptides and tested for immune response by ELISA assay using purified bacterially-produced normal and transforming ras p21 protein.

The mouse chosen for fusion had a serum titer four times higher on the transforming protein than the normal protein. Of the 2400 microtiter wells plated with fused cells, supernatants from ~700 wells tested positive to both proteins by ELISA assay; however, the supernatants in one well recognized only the transforming protein. Cells from this well were cloned and injected into mice for ascites production. The ascites fluid from this preparation called ras(53-69)Leu61 was affinity purified as described in Example 5. The ELISA titer for the ras(53-69)Leu61 antibody was $<10^2$ on normal protein while the titer on the transforming protein was $10^6$. Results are presented as the reciprocal of the maximum dilution of antiserum giving reading 5-fold above background.

Immunoblotting with Affinity Purified ras(53-69-)Leu61 Monoclonal Antibody. The affinity purified antibody was tested for reactivity with purified bacterially-produced normal and transforming ras p21 proteins in immunoblotting experiments. The migration of the purified proteins after gel electrophoresis and staining with Commassie Blue was examined and, as shown by Srivastava et al. (Proc. Natl. Acad. Sci. USA 82:38-42. 1985), the transforming protein migrates faster than the normal protein. Less intense bands were seen migrating more slowly than the normal protein and faster than the transforming protein. Doublet p21 bands were also detected by Clark et al. Proc. Natl. Acad. Sci. USA 82, 5280-5284 (1985) using rabbit polyclonal antibodies and a mouse monoclonal antibody specific for amino acid 12. The origin of lighter bands is unknown, however, they do serve as additional markers in the mixing experiment.

Proteins were immunoblotted with rabbit affinity purified H-ras(171-189) antibody which was shown to react specifically with H-ras protein (Bizub et al. Oncogene, 1987). Since the anti-H-ras peptide antiserum is directed against the variable carboxyl end of H-ras, it recognizes the transforming and normal proteins equally well; the antibody also recognized the less intense species. The reactivity of monoclonal antibody ras(53-69)Leu61 to both proteins was examined after immunoblotting. The monoclonal antibody recognized p21TLeu61 protein specifically; it failed to react with normal ras p21 even at high protein concentration. This was seen clearly in a lane where both proteins were applied.

Immunohistochemical Staining of Tissue Culture Cells. The affinity purified ras(53-69)Leu61 monoclonal antibody was used for immunohistochemical staining of tissue culture cells containing normal and mutant proteins. NIH3T3 cells (C). NIH3T3 cells transformed with c-ras$^H$Leu61, and NIH 3T3 cells transformed with the normal rat c-ras$^H$ were used. At antibody concentrations of 20 to 80 μg/ml (A,D,E), cytoplasmic staining of NIH3T3 cells transformed with c-ras$^H$Leu61 was easily detected; these cells produce ten times the amount of transforming protein relative to the normal protein in NIH3T3 cells. The staining pattern was similar to that found with rat monoclonal antibody Y13-238 and rabbit affinity H-ras(171-189) specific antibody described earlier by Bizub et al., Oncogene supra. No staining was detected if 1% BSA in PBS was used in place of the primary antibody or in normal NIH3T3 cells. NIH3T3 cells transformed by the rat c-ras$^H$ under LTR control contain about 100 times the amount of normal p21 protein compared to NIH3T3 cells. At the highest concentration of ras(53-69)Leu61 antibody (80 μg/ml) some staining was seen in these cells. However, it did not approach the intensity observed with 10 times less of the transforming protein.

Thus our analyses show that the monoclonal antibody, ras(53-69)Leu61, reacts at least $10^4$ times as well with the transforming protein relative to the normal protein in an ELISA assay, at least 10 times as well in immunoblotting experiments, and at least $10^2$ times as well in immunohistochemical staining of tissue culture cells. Immunoprecipitation procedures have not yet been refined for the ras (53-67)Leu61 antibody.

The reagent has the ability to selectively identify the transforming protein in tissue culture cells, it is useful for immunohistochemical analyses in a variety of mouse model systems of carcinogenesis. Since this sequence is the same in H-, K-, and N-ras human and mouse proteins, it is also useful for detection of all three corresponding transforming proteins in both murine and human tumors.

We claim:

1. A monoclonal antibody selectively binding for ras p21 TLeu61 transforming protein and non-cross reactive with any other ras p21 protein.

2. A monoclonal antibody which is selectively reactive with the transforming ras p21 mutant sequence elicited with an immunogenic composition comprising a peptide of the sequence

A-Leu-Asp-Ile-Leu-Asp-Thr-Ala-Gly-Leu
Glu-Glu-Tyr-Ser-Ala-Met-Arg-Asp-B                (II)

where A is H— or an amino acid having a side chain functional group capable of binding to an immunogenic carrier material and B is —OH or an amino acid having a side chain functional group capable of binding to an immunogenic carrier material.

3. The monoclonal antibody of claim 2 wherein said immunogen comprises a mixture of peptides of said sequence is used, said mixture being obtained by using a first peptide where A is cys and a second peptide where B is cys.

4. An immunometric assay for a ras p21TLeu61 transforming protein a test sample comprising reacting said sample with the monoclonal antibody of claim 1 to form a complex and determining the presence of said protein.

5. An immunometric assay for a transforming ras p21 protein sequence contained in a test sample comprising reacting said sample with the monoclonal antibody of claim 5 to form a complex and determining the presence of said protein.

6. The immunometric assay of claim 4 which is a heterogeneous assay which contains the additional step wherein the complex is separated from the reaction mixture before determining the presence of said protein.

7. The immunometric assay of claim 6 wherein an immunoblot procedure is employed, and the presence of said complex and the said selective antibody is determined by contacting said complex with a labeled second antibody.

8. The immunometric assay of claim 7 wherein said second antibody is labeled with an enzyme and a substrate for such enzyme is added, said substrate being converted by said enzyme from a non-colored to a colored state.

9. The immunometric assay of claim 4 which is a homogeneous assay.

10. The immunometric assay of claim 9 which is a competitive inhibition assay utilizing a known amount of a labeled ras p21TLeu61 protein or a subsequence thereof spanning position 61.

11. The immunometric assay of claim 4 wherein said test sample is a human biological fluid.

* * * * *

UNITED STATES PATENT AND TRADEMARK OFFICE
CERTIFICATE OF CORRECTION

PATENT NO. : 4,957,859
DATED : September 18, 1990
INVENTOR(S) : DIANE BIZUB, ELLYN FISCHBERG-BENDER, ANNA M. SKALKA It is certified that error appears in the above-identified patent and that said Letters Patent is hereby corrected as shown below:

Claim 4, line 66: after the word "protein" insert therefor -- in --.

Claim 5, line 4: delete "claim 5" and insert therefor -- claim 1 --.

Signed and Sealed this

Ninth Day of June, 1992

Attest:

DOUGLAS B. COMER

*Attesting Officer*    Acting Commissioner of Patents and Trademarks